United States Patent [19]

Inoue et al.

[11] Patent Number: 6,111,098

[45] Date of Patent: Aug. 29, 2000

[54] CRYSTAL OF PYRROLIDYLTHIOCARBAPENEM DERIVATIVE, LYOPHILIZED PREPARATION CONTAINING SAID CRYSTAL, AND PROCESS FOR PRODUCING THE SAME

[75] Inventors: Masayoshi Inoue, Toyonaka; Kazuichi Fujikane, Nishinomiya; Kenji Sugiyama, Sanda; Hideaki Tai, Osaka; Fumihiko Matsubara, Kobe; Katsuo Oda, Osaka; Takashi Oya, Tsuzuki-gun; Yoshinori Hamada, Kawanishi, all of Japan

[73] Assignee: Shionogi & Co., Ltd., Osaka, Japan

[21] Appl. No.: 08/718,543

[22] PCT Filed: Apr. 28, 1995

[86] PCT No.: PCT/JP95/00858

§ 371 Date: Oct. 9, 1996

§ 102(e) Date: Oct. 9, 1996

[87] PCT Pub. No.: WO95/29913

PCT Pub. Date: Nov. 9, 1995

[30] Foreign Application Priority Data

| May 2, 1994 | [JP] | Japan | ................................... | 6-093537 |
| May 23, 1994 | [JP] | Japan | ................................... | 6-108554 |

[51] Int. Cl.$^7$ .............................................. C07D 477/20
[52] U.S. Cl. .............................................. 540/350
[58] Field of Search ............................................. 540/350

[56] References Cited

U.S. PATENT DOCUMENTS

| 3,697,506 | 10/1972 | Butler | 260/239.1 |
| 4,029,655 | 6/1977 | Cise | 260/243 C |
| 4,104,391 | 8/1978 | Cise | 424/246 |
| 4,146,971 | 4/1979 | Bornstein et al. | 34/5 |
| 4,432,987 | 2/1984 | Barth et al. | 424/271 |
| 4,748,238 | 5/1988 | Shih | 540/350 |
| 4,966,899 | 10/1990 | Kohno et al. | 514/197 |
| 5,286,856 | 2/1994 | Kaneko et al. | 540/350 |
| 5,424,069 | 6/1995 | Kaneko et al. | 424/400 |
| 5,539,102 | 7/1996 | Sendo et al. | 540/310 |

FOREIGN PATENT DOCUMENTS

| 0528678 | 2/1993 | European Pat. Off. . |
| 60-19758 | 5/1985 | Japan . |
| 60-19759 | 5/1985 | Japan . |
| 61-129123 | 6/1986 | Japan . |
| 61-172878 | 8/1986 | Japan . |
| 61-43356 | 9/1986 | Japan . |
| 63-174927 | 7/1988 | Japan . |
| 64-79180 | 3/1989 | Japan . |
| 3-74643 | 11/1991 | Japan . |
| 4-59730 | 2/1992 | Japan . |
| 4-66202 | 10/1992 | Japan . |
| 4-338332 | 11/1992 | Japan . |
| 5-271241 | 10/1993 | Japan . |
| 5-294970 | 11/1993 | Japan . |

OTHER PUBLICATIONS

CRC Handbook, 62nd edition (CRC Press), p. F–101, 1974.

Primary Examiner—Mark L. Berch
Attorney, Agent, or Firm—Fish & Neave; James F. Haley, Jr.; Karen E. Brown

[57] ABSTRACT

The present invention provides a crystal of (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid represented by the following formula, a lyophilized preparation comprising the crystal, and a process for producing the same. The production process comprises the steps of freezing an aqueous solution containing the above-mentioned compound by cooling to −20° C. or lower; warming the frozen solution to 0 to −10° C.; and cooling and warming the frozen solution at least twice in a temperature range of 0 to −10° C.

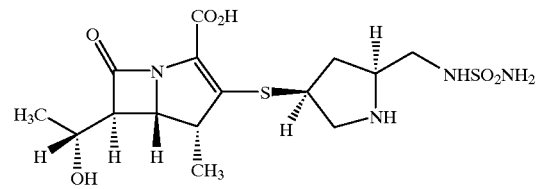

20 Claims, 2 Drawing Sheets

CRYSTAL OF PYRROLIDYLTHIOCARBAPENEM DERIVATIVE, LYOPHILIZED PREPARATION CONTAINING SAID CRYSTAL, AND PROCESS FOR PRODUCING THE SAME

This application is a 371 of PCT/JP95/00858, filed Apr. 28, 1995.

TECHNICAL FIELD

The present invention relates to a crystal of pyrrolidylthiocarbapenem derivative excellent in storage stability and solubility, a lyophilized preparation containing the crystal and a process for producing the same.

BACKGROUND ART (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid represented by the following formula (hereinafter referred to as S-4661 in the specification) is a pyrrolidylthiocarbapenem derivative. S-4661 is a useful compound as an antimicrobial drug, and orally or parenterally administered.

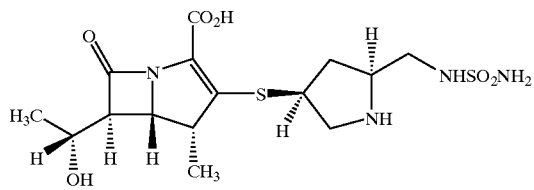

S-4661 itself is described in Japanese Laid-Open Patent Publication (Kokai) No. 5-294970. However, no crystal of S-4661 is described in the Publication. When S-4661 is produced, conventionally, a process for producing it in an amorphous form only is known. However, an amorphous solid of S-4661 has insufficient stability during storage. Therefore, when S-4661 is stored under ordinary storage conditions for a long period, the color thereof is changed, and the purity disadvantageously deteriorates. Thus, it is desired to prepare a crystalline preparation of S-4661 having a higher storage stability than an amorphous preparation. In particular, among the crystalline preparations, a preparation containing an inner salt is more preferable in that it is unnecessary to use an additive in a large amount in order to form a salt.

Furthermore, among the crystalline preparations of S-4661, a crystalline lyophilized preparation is preferable, because it is generally easy to ensure sterility of a lyophilized preparation and to remove particulate matters from the lyophilized preparation.

As a general process for producing a lyophilized preparation, a variety of processes are conventionally known. For example, Japanese Laid-Open Patent Publication (Kokai) Nos. 61-172878, 63-174927 and 4-59730 disclose that NaCl is added to a solution before lyophilization in order to improve solubility and stability of an amorphous lyophilized preparation. Japanese Laid-Open Patent Publication (Kokai) No. 4-338332 discloses that $Na_2CO_3$ or $NaHCO_3$ is added to a drug in a form of a hydrochloride salt so that an insoluble free base is not deposited.

The following processes are known as a process for obtaining a crystalline lyophilized preparation: for example, Japanese Patent Publication (Kokoku) No. 4-66202 discloses that an aqueous solution of a drug is allowed to be in a supercooled state without freezing, and crystal nuclei are generated in the supercooled state; Japanese Patent Publication (Kokoku) No. 60-19758 discloses that an aqueous solution of a drug containing 2 to 25 v/v % of alcohol is gradually cooled to freeze water and crystal nuclei are generated in a state of a concentrated alcohol solution; and Japanese Patent Publication (Kokoku) Nos. 60-19759, 03-74643 and Japanese Laid-Open Patent Publication (Kokai) No. 5-271241 disclose that an aqueous solution of a drug is frozen at a predetermined temperature, then warmed to a predetermined temperature, and retained at a constant temperature.

Conditions suitable for lyophilization are varied depending on the drugs to be lyophilized. Therefore, the aforementioned known processes are not necessarily suitable for a process for producing a lyophilized preparation containing the crystal of S-4661. For example, since the process for lyophilization by freezing an aqueous solution containing S-4661 at a predetermined temperature and retaining it at a constant temperature takes a very long time, it is not suitable as an industrial process.

As described above, no process suitable to obtain a crystal of S-4661, in particular, an inner salt crystal, and no lyophilization process suitable to obtain a lyophilized preparation containing the crystal have been found yet.

DISCLOSURE OF THE INVENTION

A crystal of S-4661 of the present invention is a crystal of pyrrolidylthiocarbapenem derivative S-4661 represented by the following formula.

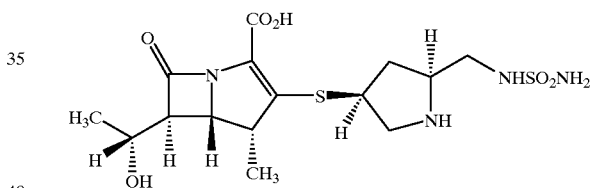

A lyophilized preparation containing the above-mentioned crystal is also in the scope of the present invention.

The process for producing a lyophilized preparation according to the present invention comprises the steps of freezing an aqueous solution containing S-4661 by cooling to −20° C. or lower; warming the frozen solution to 0 to −10° C.; and cooling and warming the frozen solution at least twice in the temperature range of 0 to −10° C.

The present invention provides a crystal of S-4661 excellent in storage stability and solubility, and having a high industrial applicability. Furthermore, the present invention provides a lyophilized preparation containing the crystal of S-4661, excellent in storage stability and reconstitution property.

BEST MODE FOR CARRYING OUT THE INVENTION

Figure 1:
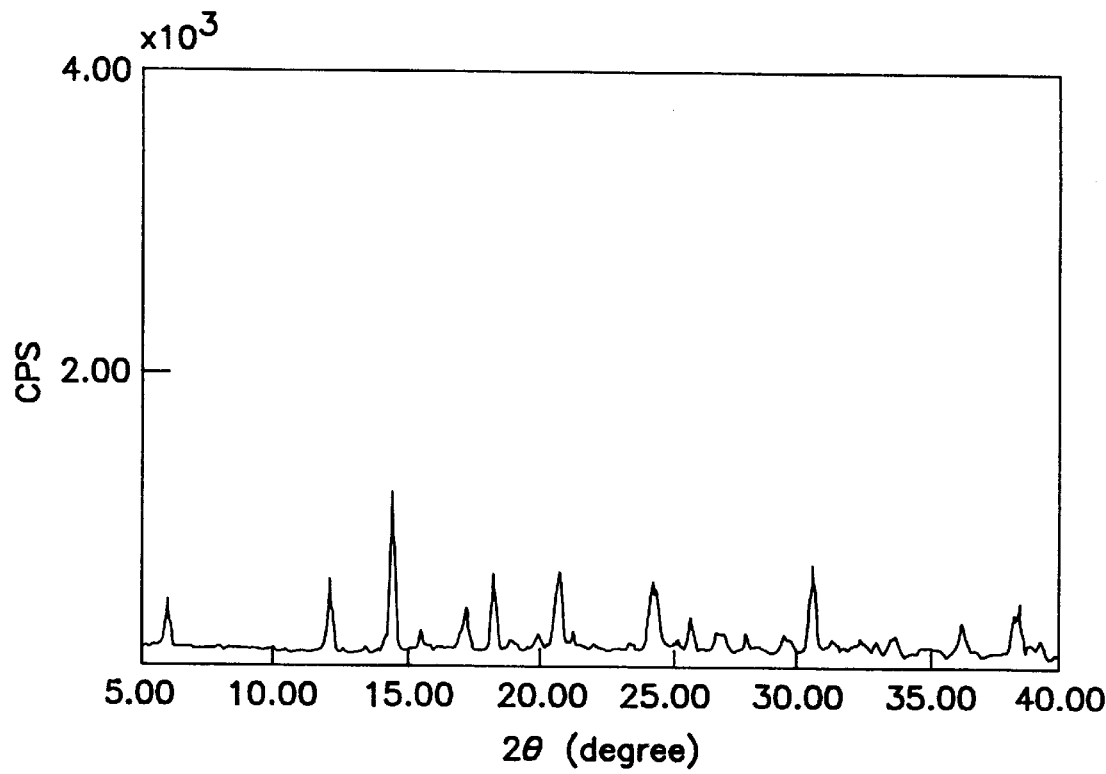
FIG. 1 is a powder X-ray diffraction chart of a lyophilized product of S-4661 obtained in Example 3.

A crystal of S-4661 of the present invention is a crystal of pyrrolidylthiocarbapenem derivative S-4661 represented by the following formula.

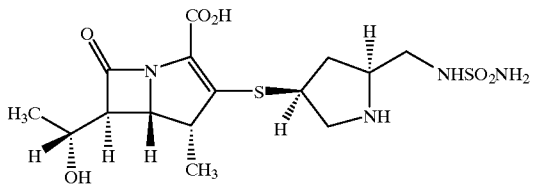

The crystal of S-4661 is preferably an inner salt crystal. The inner salt crystal of S-4661 is believed to be a betaine structure represented by the following formula.

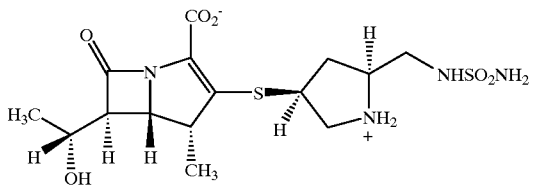

Such an inner salt crystal is more preferable in that it has a pure form containing no counter ion other than a desired component, unlike the case of an Na salt and the like.

The results of measurements by a powder X-ray diffraction method reveal that two different crystal forms exist for a crystal of S-4661. Hereinafter, the two crystal forms are referred to as Type I and Type II. Type I crystal and Type II crystal are identified by characteristic peaks obtained by the powder X-ray diffraction method. Diffraction angles (2θ) of the characteristic main peaks of the respective crystal forms are shown below.

Type I: 7.32, 14.72, 16.62, 20.42, 21.1, 22.18, 23.88 and 29.76 (degree)

Type II: 6.06, 12.2, 14.56, 17.0, 18.38, 20.68, 24.38, 24.60, 25.88 and 30.12 (degree)

(X ray-diffraction measurement conditions: CuKα line, 1.54 Å (monochromator), a tube voltage 40 kV, a tube current 40 mA) The crystal structure of S-4661 described above is novel knowledge.

In the case where the crystal of the present invention is used as an aqueous solution, for example, used for an injection, Type II crystal is more preferable to Type I crystal in that the dissolution rate of Type II crystal is higher.

The crystal of S-4661 of the present invention can be obtained by a method such as recrystallization, but can also be obtained in a form contained in a lyophilized preparation and the like.

In order to obtain the crystal of S-4661 of the present invention by recrystallization, S-4661 is crystallized from an organic solvent such as alcohol and acetone, water, or a mixed solution thereof. Examples of alcohol used herein include methanol, ethanol, isopropanol and the like. In the case where a mixed solvent of an organic solvent and water is used, a mixing ratio of water to the organic solvent is preferably 1:1 to 1:5 (v/v). In order to obtain the crystal of the present invention, S-4661 is dissolved in the organic solvent, water, or the mixed solvent to prepare an S-4661 solution. A concentration of the S-4661 solution is preferably about 5 to 40 percent by weight. In order to deposit the crystal of S-4661 from the solution, any crystallization operation such as cooling and/or stirring can be performed. Crystals of S-4661 can be preferably obtained by stirring the solution while cooling it to about 0 to 10° C.

The crystals of the present invention may be polymorphism, but can be obtained in the form of a single crystal by controlling crystallization conditions. In order to obtain Type I crystal, for example, S-4661 is crystallized from water or a water/ethanol system. On the other hand, Type II crystal can be obtained by crystallization from water, but preferably crystallized from a water/isopropanol system, and more preferably, the water/isopropanol system is a mixed solution of water and isopropanol in proportion of 1:3 (v/v).

Although a water content of the crystals of the present invention is not necessarily constant but varied depending on drying conditions and storage conditions, crystals of Type I generally tend to be stabilized with water content in the range of about 0 to 5.0% at room temperature. Type II crystal may be stabilized with water content in a ratio of up to about 10% at room temperature. In either case of any water content, however, the characteristic diffraction angles (2θ) in X-ray diffraction patterns are not changed, but the characteristic peaks described above are present. An amount of an organic solvent which remains in the crystals is not constant in either type of the crystal, but varied depending on the crystallization method and drying conditions.

The crystal of S-4661 of the present invention can be obtained as a lyophilized preparation. Hereinafter, the lyophilized preparation containing the crystal of S-4661 may be simply referred to as a crystalline lyophilized preparation. The crystalline lyophilized preparation of the present invention can contain either one of the two types of crystal, i.e., Type I crystal and Type II crystal, or a mixture thereof. In the case where the crystalline lyophilized preparation of the present invention contains the two types of crystals as a mixture, each crystal can be contained in an arbitrary proportion.

A lyophilized preparation containing the crystal of S-4661 can be preferably obtained by the following process. The process comprises the steps of freezing an aqueous solution containing S-4661 by cooling to −20° C. or lower; warming the frozen solution to 0 to −10° C.; and cooling and warming the frozen solution at least twice in the temperature range of 0 to −10° C. This process is one aspect of the present invention.

In order to obtain a crystalline lyophilized preparation of S-4661 by the process of the present invention, first, an aqueous solution of S-4661 is prepared. S-4661 can be synthesized by a known process and be in any state such as a crystal, amorphous, a hydrate, a solvate, and a mixture thereof. The aqueous solution of S-4661 can contain S-4661 at a concentration of about 8 to 17 percent by weight. The pH of the aqueous solution is about 5.8 to 6.2, and preferably, 5.8 to 6.0 in terms of stability of S-4661. In order to adjust the pH to be in the aforementioned pH range, any base and/or basic salt can be added to the aqueous solution as a pH adjusting agent. The base and/or basic salt is preferably at least one compound selected from the group consisting of NaOH, $Na_2CO_3$ and $NaHCO_3$. Although an addition amount thereof is varied depending on the compound to be added and the concentration of S-4661 and the like, for example, in the case of $Na_2CO_3$, an appropriate amount is about 0.1 percent by weight (about 0.005 in molar ratio) to S-4661, for example, about 0.67 mg for 500 mg of S-4661.

The aqueous solution can further contain an inorganic salt. Examples of the inorganic salt include alkali metal halide salts such as NaCl, NaBr, KCl, and alkali metal sulfate salts such as $Na_2SO_4$. NaCl and $Na_2SO_4$ are preferable, and NaCl is more preferable. Preferably, the inorganic salt can be added to the aqueous solution in an amount of about 0.01 to 0.22 moles, and more preferably about 0.02 to 0.13 moles, per mole of S-4661. In the case where the inorganic salt is NaCl, the addition amount is preferably about 0.15 to 5 parts by weight, and more preferably about 0.3 to about 3 parts by weight to 100 parts by weight of S-4661. For example, preferably about 0.75 to 25 mg, and more preferably about 1.5 to about 15 mg of NaCl is added to 500 mg of S-4661.

The thus prepared aqueous solution containing S-4661 is frozen by cooling to $-20°$ C. or lower, and preferably $-30$ to $-40°$ C. Such cooling step is performed, preferably over 1 to 2 hours. This process is herein referred to as first freezing or a first freezing step. Prior to the first freezing step, the prepared aqueous solution of S-4661 may be allowed to stand at room temperature for several hours, preferably 1 to 2 hours.

A frozen solution obtained in the first freezing step is then warmed to 0 to $-10°$ C., preferably $-2$ to $-10°$ C., and more preferably $-3$ to $-5°$ C. Such warming step is performed preferably over 0.5 to 1.5 hours. Then the warmed frozen solution is further cooled and warmed repeatedly in the range of 0 and $-10°$ C. The operation of warming and cooling is performed at least twice, preferably 2 to 10 times. The expression "warming and cooling" refers to not only the case where the solution is first warmed and then cooled, but includes the case where the solution is first cooled and then warmed. Preferably, the solution is warmed and cooled in the temperature range of 1 to 5 K, more preferably 1 to 3 K. The warming rate and cooling rate is preferably 8 to 12 K/hour. The repetition of warming and cooling is preferably performed in a continuous manner, and preferably over 5 hours to 10 hours. Preferably, after the step of warming and cooling, the frozen solution is further allowed to stand at about $-3$ to $-10°$ C., preferably $-5$ to $-10°$ C. for 1 to 10 hours, preferably 3 to 8 hours. Crystals of S-4661 are deposited by the steps of warming the frozen solution, repeating the operation of warming and cooling, and optionally allowing the frozen solution to stand. The process including these steps all together after the first freezing is herein referred to as crystallization or a crystallization step.

The thus obtained crystalline frozen product is subjected to vacuum drying according to an conventional method, so as to obtain a crystalline lyophilized preparation of S-4661.

In the case where S-4661 is lyophilized without being crystallized, in general, a collapse temperature of a frozen phase is about $-15°$ C. On the other hand, in the case where S-4661 is lyophilized after crystals of S-4661 are deposited, a an eutectic point of the frozen phase is about $-0.5°$ C. In other words, by crystallizing S-4661, lyophilization can be caused at a higher temperature. When stability of the obtained lyophilized preparation was tested, it was confirmed that the crystalline lyophilized preparation has a higher stability than an amorphous lyophilized preparation.

As described above, in the process of the present invention, the pH of an aqueous solution containing S-4661 is preferably adjusted to about 5.8 to 6.2. By doing this, the stability of S-4661 in the aqueous solution can be improved. An addition amount of a pH adjusting agent is as small as about 0.005 to 0.01 moles per mole of S-4661. Thus, even if a base is added as the pH adjusting agent, S-4661 is not converted to a salt corresponding to the base (e.g., an Na salt in the case where NaOH is added). Accordingly, the pH adjusting agent can be added even when an inner salt of S-4661 is desired. The aforementioned Japanese Laid-Open Patent Publication (Kokai) No. 4-338332 discloses the addition of $Na_2CO_3$ or $NaHCO_3$. However, these bases are added to a drug which is a hydrochloride salt for the purpose of not depositing the drug in the form of a free base. For this reason, the addition amount is as relatively large as 0.5 to 5 equivalents to the drug. Therefore, in this case, the drug is believed to be in the form of an Na salt. Thus, the base is used for a different purpose than in the process of the present invention where the base is used as a pH adjusting agent.

Furthermore, according to the present invention, an inorganic salt is preferably added to an aqueous solution containing S-4661 in order to facilitate crystallization. In the conventional lyophilization process where the condition of warming and cooling is not defined, when an inorganic salt is added, an adverse effect is caused in crystallization in that an amorphous portion in a resulting lyophilized preparation is increased. In the process of the present invention, however, the addition of the inorganic salt does not cause such an adverse effect in crystallization. Since the inorganic salt is added at a significantly low concentration, the conversion of S-4661 to the inorganic salt does not occur. On the other hand, in Japanese Laid-Open Patent Publication (Kokai) Nos. 61-172878, 63-174927 and 4-59730 which disclose the addition of the inorganic salt, the inorganic salt is added in order to improve solubility and stability of an amorphous lyophilized preparation. Thus, the inorganic salt is added at a high concentration, i.e, a molar ratio of 0.2 or more in all the Publications. The pH adjusting agent described above is believed to have the same function as the inorganic salt as well as the function of adjusting pH.

Furthermore, according to the present invention, a lyophilized preparation can be obtained without using an organic solvent, so that no problems such as a residual solvent arise, thus leading to an advantage of safety.

The present invention provides a crystalline lyophiled preparation containing either one of the two types of crystals of S-4661, i.e., Type I crystal and Type II crystal, or a mixture thereof. Which of the crystal the lyophilized preparation contains, or in what ratio the respective crystal forms are present in the crystalline lyophilized preparation containing the mixture of Type I and Type II crystals is determined by various conditions such as the pH adjusting agent, the types of added inorganic salt, the concentration and temperature conditions in each step. In order to more selectively obtain Type II crystal, for example, NaCl is added, preferably in an amount of 0.6 percent by weight or more, more preferably 2 percent by weight or more, and still more preferably 3 percent by weight or more. Then, crystallization is performed by raising and lowering the temperature in a temperature range of $-2°$ C. to $-10°$ C., preferably $-3°$ C. or lower. Alternatively, in the case where crystallization is performed after an aqueous solution of S-4661 is prepared and allowed to stand at room temperature for several hours, it is preferred that the solution with NaCl added in an amount of 2 percent by weight or more is used and the crystallization is performed at $-2°$ C. or lower.

In the case where Type I crystal is desired, for example, conditions can be as follows: mannitol is added in place of the inorganic salt; or the pH is adjusted to be in the vicinity of 6 by using a phosphate buffer without adding the inorganic salt.

The lyophilized preparation of the present invention can be used as an aqueous solution for use as an injection or the like. In this case, as described above, Type II crystal is preferable to Type I crystal in that Type II crystal has a higher dissolution rate in water. The dissolution rate can be further improved by adding mannitol to the preparation. The mannitol is added to an aqueous solution for preparing a lyophilized preparation, in an amount of 5 parts by weight or more, preferably 10 parts by weight or more, more preferably 15 parts by weight or more, and most preferably 15 to 50 parts by weight on the basis of 100 parts by weight of S-4661.

EXAMPLES

Hereinafter, the present invention will be described by way of examples.

Example 1
Preparation of Type I crystal

A 25 wt % aqueous solution of S-4661 was prepared. The aqueous solution was stirred in an ice bath to obtain a targeted product by recrystallization. The product was dried under reduced pressure at room temperature for 20 hours in a desiccator. As a result of powder X-ray diffraction measurement, it was confirmed that the obtained crystal is Type I crystal of an inner salt. For the obtained crystal, element analysis, water quantity measurement (Karl Fischer's method), and IR measurement were performed. The results are shown below.

Element analysis (calculated as $C_{15}H_{24}N_4O_6S_2 \cdot \frac{1}{2}H_2O$) Calculated values: C,41.95%; H,5.87%; N,13.04%; S,14.93% Analytical values: C,41.94%; H,5.95%; N,13.14%; S,14.75% $H_2O$(KF method): 2.14% (calculated value 2.10%)

IR($cm^{-1}$)(Nujol): 3460,3255,3120,1763,1620,1555,1378, 1325

Example 2
Preparation of Type II crystal

Isopropanol was added in an amount about three times as much on the basis of volume to a 10 wt % aqueous solution of S-4661. The solution was stirred in an ice bath to obtain a targeted product by recrystallization. The product was dried under reduced pressure at room temperature for 40 hours in a desiccator. As a result of powder X-ray diffraction measurement, it was confirmed that the obtained crystal is Type II crystal of an inner salt. For the obtained crystal, element analysis, water quantity measurement (Karl Fischer's method), and IR measurement are performed. The results are shown below.

Element analysis (calculated as $C_{15}H_{24}N_4O_6S_2 \cdot 1.65H_2O$) Calculated values: C,40.00%; H,6.11%; N,12.44%; S,14.23% Analytical values: C,39.76%; H,6.15%; N,12.56%; S,14.16% $H_2O$ (KF method): 6.65% (calculated value 6.60%)

IR($cm^{-1}$)(Nujol): 3540,3465,3180,1748,1625,1560,1457, 1150

Hereinafter, preparation examples of the crystalline lyophilized preparation of the present invention are shown in Examples 3 to 14.

Example 3

NaOH and NaCl were added to a 10 wt % aqueous solution of S-4661 so as to be contained in an amount of 0.07 percent by weight and 0.6 percent by weight on the basis of S-4661, respectively. The resulting aqueous solution was cooled to −30° C. over 1 hour to be frozen (the first freezing step). The frozen solution was warmed, and the operation of cooling and warming was performed 4 times in the temperature range of −3.5 to −6° C. over 4 hours. The operation of cooling and warming was performed at a rate of about 10 K/hour. After the repeated operation of cooling and warming, the frozen solution was allowed to stand at −5.5° C. for 5 hours (crystallization step). After crystallization, vacuum drying was performed according to a conventional method to obtain a crystalline lyophilized product of S-4661. Herein, vacuum drying conditions are as follows:

First drying conditions: shelf temperature +20° C., 19 hours, degree of vacuum 0.1 hPa.

Second drying conditions: shelf temperature +40° C., 5 hours, degree of vacuum 0.02 hPa.

Example 4

NaOH and NaCl were added to an 8 wt % aqueous solution of S-4661 so as to be contained in an amount of 0.07 percent by weight and 0.6 percent by weight on the basis of S-4661, respectively. The resulting aqueous solution was cooled to −30° C. over 1 hour to be frozen. The frozen solution was warmed, and the operation of cooling and warming was performed 5 times in the temperature range of −3.5 to −6° C. over 5 hours. The repeated operation of cooling and warming was performed at a rate of about 10 K/hour. After the repeated operation of cooling and warming, the frozen solution was allowed to stand at −7° C. over 5 hours. After the crystallization, vacuum drying was performed in the same manner as in Example 3 to obtain a crystalline lyophilized product of S-4661.

Example 5

NaOH and NaCl were added to a 10% aqueous solution of S-4661 so as to be contained in an amount of 0.07 percent by weight and 0.6 percent by weight on the basis of S-4661, respectively. The resulting aqueous solution was cooled to −30° C. over 1 hour to be frozen. The frozen solution was warmed, and the operation of cooling and warming was performed 5 times in the temperature range of −4.0 to −8° C. over 5 hours. The repeated operation was performed at a rate of about 10 K/hour. After the repeated operation of cooling and warming, the frozen solution was allowed to stand at −5° C. for 5 hours. After crystallization, vacuum drying was performed in the same manner as in Example 3 to obtain a lyophilized product of S-4661.

Examples 6 to 14

A crystalline lyophilized product of S-4661 was obtained in the same manner as in Example 3 except that the concentration of S-4661, the types and the addition amount of a pH adjusting agent, the addition amount of an inorganic salt, and crystallization conditions shown in Table 1 were adopted.

TABLE 1

| Example | S-4661 Concentration | pH controlling agent (Addition amount) | Salt (Addition amount) | Crystallization conditions | | Crystal form |
|---|---|---|---|---|---|---|
| 3 | 10% | NaOH (0.07%) | NaCl (0.6%) | −3.5∼−6° C. −5.5° C. | 4 hours 5 hours | II |
| 4 | 8% | NaOH (0.07%) | NaCl (0.6%) | −3.5∼−6° C. −7° C. | 5 hours 5 hours | II |
| 5 | 10% | NaOH (0.07%) | NaCl (0.6%) | −4.0∼−8° C. −5° C. | 5 hours 5 hours | II |
| 6 | 8% | $Na_2CO_3$ (0.13%) | NaCl (0.3%) | −1.5∼−6° C. −5° C. | 5 hours 5 hours | I |
| 7 | 10% | $Na_2CO_3$ (0.13%) | NaCl (0.6%) | −1.5∼−6° C. −5° C. | 5 hours 5 hours | I |
| 8 | 10% | NaOH (0.07%) | not added | −3.5∼−6° C. −5° C. | 5 hours 5 hours | I |
| 9 | 10% | $NaHCO_3$ (0.3%) | not added | −5.5∼−7.5° C. −5° C. | 5 hours 5 hours | I |
| 10 | 10% | $NaHCO_3$ (0.3%) | NaCl (0.6%) | −3.5∼−6° C. −5° C. | 5 hours 5 hours | I |
| 11 | 8% | $Na_2CO_3$ (0.13%) | NaCl (0.3%) | −3.5∼−6° C. −5° C. | 5 hours 5 hours | I |
| 12 | 10% | $Na_2CO_3$ (0.13%) | NaCl (0.6%) | −3.5∼−6° C. −10° C. | 5 hours 5 hours | I |
| 13 | 10% | $NaHCO_3$ (0.3%) | NaCl (1%) | −2.5∼−4.5° C. −4° C. | 5 hours 5 hours | I |
| 14 | 10% | $NaHCO_3$ (0.3%) | NaCl (2%) | −2.5∼−4.5° C. −4° C. | 5 hours 5 hours | II |

Comparative Example 1

NaCl was added to an 8 wt % aqueous solution of S-4661 so as to be contained in an amount of 5 percent by weight on the basis of S-4661. The resulting aqueous solution was cooled to −30° C. over 1 hour to be frozen. After freezing, vacuum drying was performed according to a conventional method to obtain an amorphous lyophilized product of S-4661. Herein, vacuum drying conditions are as follows:

First drying conditions: shelf temperature −20° C., 83 hours, degree of vacuum 0.08 hPa.

Second drying conditions: shelf temperature 60° C., 5 hours, degree of vacuum 0.02 hPa.

Comparative Example 2

An amorphous lyophilized product of S-4661 was obtained in the same manner as in Comparative Example 1 except that NaCl was added so as to be contained in an amount of 15 percent by weight on the basis of S-4661.

Comparative Example 3

An amorphous lyophilized products of S-4661 was obtained in the same manner as in Comparative Example 1 except that NaCl was not added.

Comparative Example 4

S-4661 was dissolved in a 3 wt % aqueous solution of ethyl acetate so as to be contained in an amount of 20 percent by weight. The resulting solution was rapidly cooled by acetone dry ice to be frozen at −70° C. After freezing, crystallization was performed at −5° C. for 10 hours, and after the crystallization, freezing was again performed at −70° C. After freezing, vacuum drying was performed according to a conventional method to obtain a lyophilized product of S-4661. Drying at this time was performed by spontaneously warming the shelf temperature to room temperature for 16 hours at a degree of vacuum of 0.02 hPa.

Comparative Example 5

A lyophilized product of S-4661 was obtained in the same manner as in Comparative Example 3 except that a 2 wt % aqueous solution of ethanol was used.

Comparative Example 6

A lyophilized preparation of S-4661 was obtained in the same manner as in Comparative Example 3 except that a 2 wt % aqueous solution of isopropanol was used.

Example 15

X-ray diffraction measurement

Figure 2:
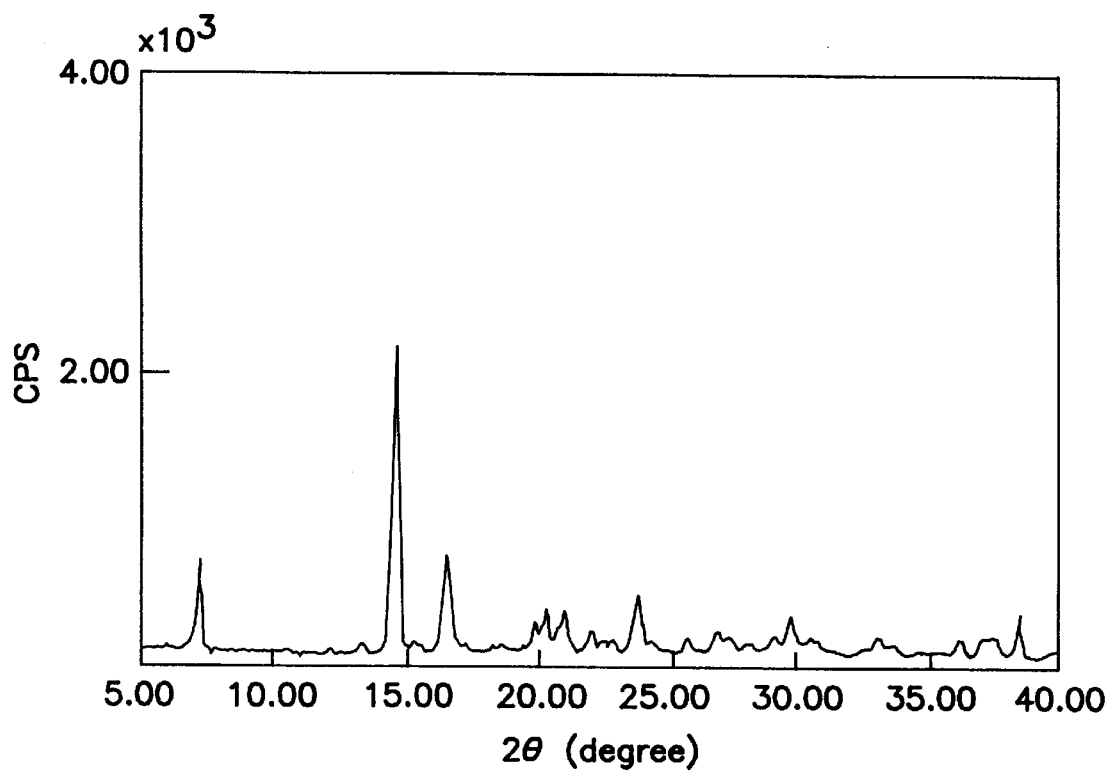
FIG. 2 is a powder X-ray diffraction chart of a lyophilized product of S-4661 obtained in Example 8.
Figure 3:
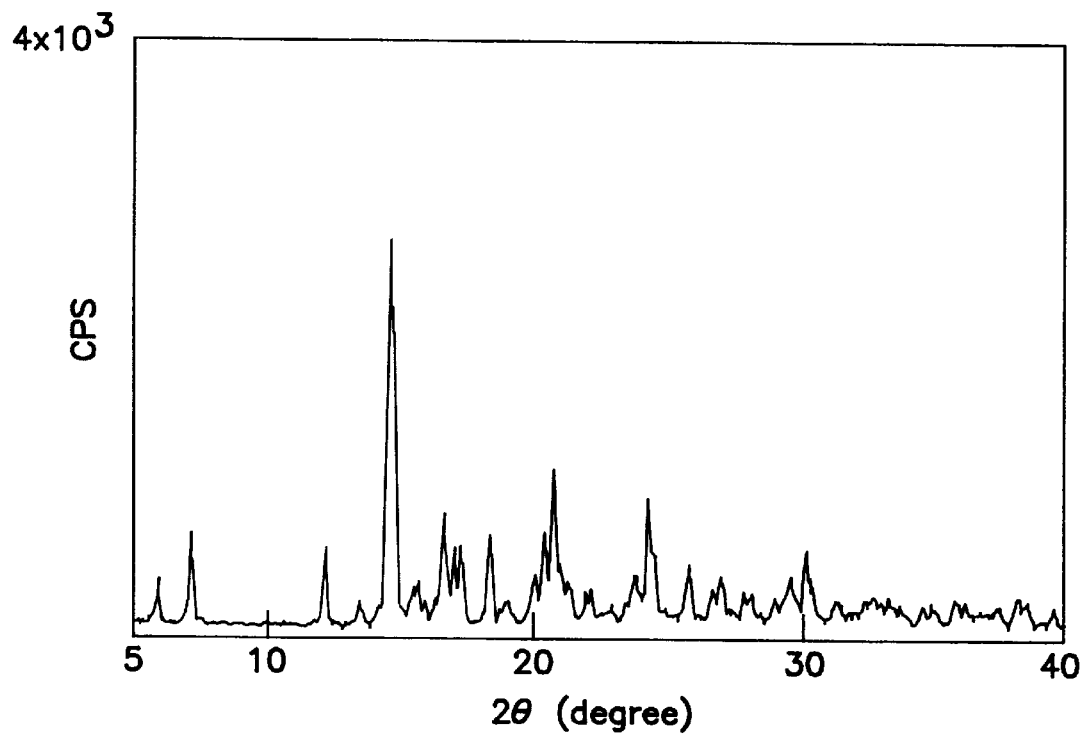
FIG. 3 is a powder X-ray diffraction chart of a lyophilized product of S-4661 obtained in Example 13.
Figure 4:
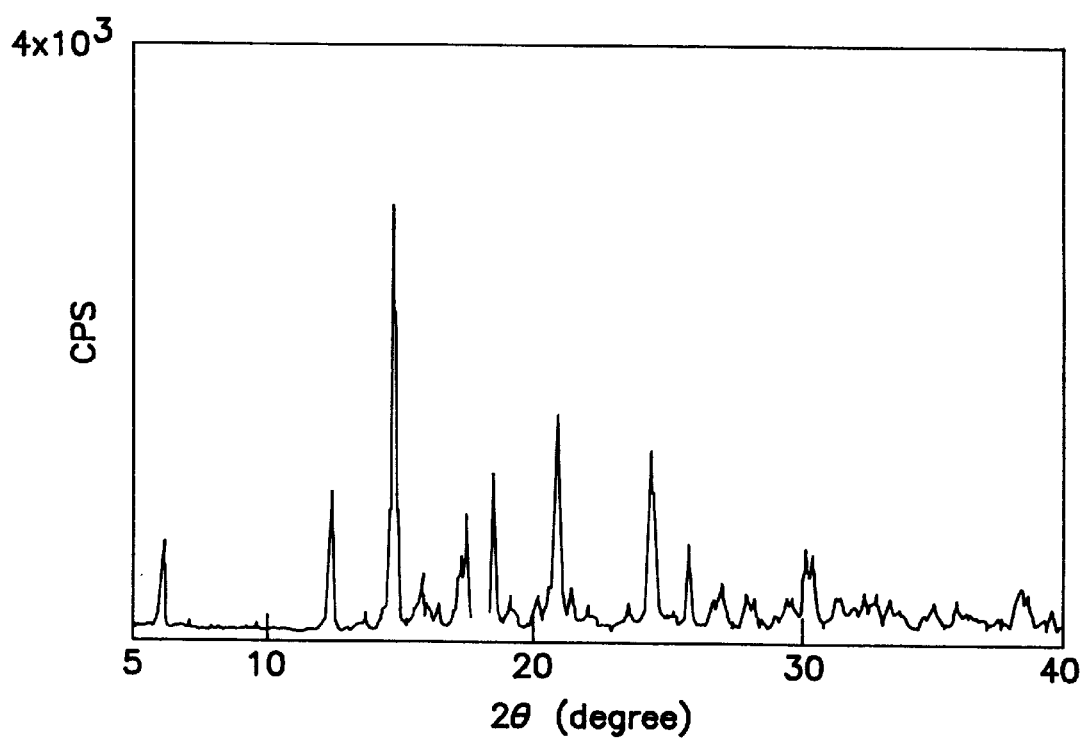
FIG. 4 is a powder X-ray diffraction chart of a lyophilized product of S-4661 obtained in Example 14.

Powder X-ray diffraction measurement was performed for the lyophilized products obtained in Examples 3 to 14 and Comparative Examples 1 to 6. X-ray diffraction charts of the crystalline lyophilized products of Examples 3, 8, 13 and 14 are shown in FIGS. 1, 2, 3 and 4. X-ray diffraction angles of the lyophilized products obtained in Examples 3 to 5 and 8 are shown in Table 2. Type II crystal was obtained in Examples 3 to 5 and 14, whereas Type I crystal was obtained in Examples 6 to 13. The identified crystal form is shown in Table 1 above. Whether the contained crystal was Type I or Type II was identified by the characteristic peaks shown below.

Type I: $2\theta$=7.32, 14.72, 16.62, 20.42, 21.1, 22.18, 23.88 and 29.76 (degree)

Type II: $2\theta$=6.06, 12.2, 14.56, 17.0, 18.38, 20.68, 24.38, 24.60, 25.88 and 30.12 (degree)

These peaks were matched with the X-ray diffraction patterns of crystals of Type I and II obtained in Examples 1 and 2. The obtained lyophilized products were all inner salt crystals.

TABLE 2

| Example | Diffraction intensity | Diffraction angle (2θ) | Crystal form |
|---|---|---|---|
| 3 | strong | 6.0 | Type II |
|  |  | 12.2 |  |
|  |  | 14.5 |  |
|  | medium-weak | 17.3 |  |
|  |  | 20.8 |  |
|  |  | 24.4 |  |
|  |  | 24.5 |  |
|  |  | 30.5 |  |

TABLE 2-continued

| Example | Diffraction intensity | Diffraction angle (2θ) | Crystal form |
|---|---|---|---|
| 4 | strong | 6.1 | Type II |
| | | 12.2 | |
| | | 14.4 | |
| | medium-weak | 17.3 | |
| | | 18.4 | |
| | | 20.7 | |
| | | 24.4 | |
| | | 24.6 | |
| | | 30.4 | |
| 5 | strong | 6.1 | Type II |
| | | 12.2 | |
| | | 14.6 | |
| | medium-weak | 17.3 | |
| | | 18.4 | |
| | | 20.8 | |
| | | 24.4 | |
| | | 24.6 | |
| | | 30.5 | |
| 8 | strong | 7.3 | Type I |
| | | 14.7 | |
| | | 16.6 | |
| | medium-weak | 19.9 | |
| | | 20.4 | |
| | | 21.0 | |
| | | 22.2 | |
| | | 29.6 | |

Example 16

Relationship between a pH adjusting agent and the addition amount of salts, and the resulting crystal form As shown in Tables 3 to 5 below, crystalline lyophilized products of S-4661 were obtained by varying the types and the addition amounts of the pH adjusting agent and the added salts. In Tables 3 to 5, "addition concentration" refers to a molar concentration relative to a 10 wt % aqueous solution of S-4661, and "addition amount" refers to wt % to S-4661. Crystallization was performed by raising and lowering the temperature in the range of −3 to −4° C. over 5 hours, and further allowing the solution to stand at −5° C. for 5 hours. The crystal form thereof was confirmed by X-ray diffraction measurement of the obtained lyophilized products. In the Tables, II>I indicates a mixture containing Type II crystal in a larger amount, II>>I indicates a mixture containing crystals mainly consisting of Type II, and II≧I indicates a mixture containing Type II crystal in a slightly larger amount. The relationship between the amount of Type I crystal and that of Type II crystal was evaluated from a peak area ratio of the respective peaks at 2θ=7.3 and 6.0.

TABLE 3

| | Inorganic salt | NaCl | Na$_2$SO$_4$ | NaBr |
|---|---|---|---|---|
| pH controlling agent (pH 6) | Addition concentration | 10 mM | 7.5 mM | 10 mM |
| | Addition amount | 0.6% | 1.1% | 1.0% |
| Sodium sulfite | Addition concentration | 4.0 mM | 4.0 mM | 4.0 mM |
| | Addition amount | 0.5% | 0.5% | 0.5% |
| | Crystal form | II > I | I > II | I ≧ II |

TABLE 3-continued

| | Inorganic salt | NaCl | Na$_2$SO$_4$ | NaBr |
|---|---|---|---|---|
| Disodium phosphate | Addition concentration | 2.5 mM | 2.5 mM | 2.5 mM |
| | Addition amount | 0.4% | 0.4% | 0.4% |
| | Crystal form | II > I | I | I ≧ II |
| Sodium acetate | Addition concentration | 45.7 mM | 45.7 mM | 45.7 mM |
| | Addition amount | 3.8% | 3.8% | 3.8% |
| | Crystal form | II | II >> I | II |
| Disodium succinate | Addition concentration | 12.3 mM | 12.3 mM | 12.3 mM |
| | Addition amount | 2.0% | 2.0% | 2.0% |
| | Crystal form | II | I > II | I ≧ II |
| Trisodium citrate | Addition concentration | 4.8 mM | 5.8 mM | 4.8 mM |
| | Addition amount | 1.3% | 1.5% | 1.3% |
| | Crystal form | I >> II | I | I >> II |
| Sodium benzoate | Addition concentration | 156.1 mM | 156.1 mM | 138.8 mM |
| | Addition amount | 22.5% | 22.5% | 20.0% |
| | Crystal form | II | II > I | I >> II |
| Lysine | Addition concentration | 2.1 mM | 2.1 mM | 2.1 mM |
| | Addition amount | 0.3% | 0.3% | 0.3% |
| | Crystal form | II | II >> I | II >> I |
| Tris-amino-methane | Addition concentration | 2.5 mM | 2.5 mM | 2.1 mM |
| | Addition amount | 0.3% | 0.3% | 0.3% |
| | Crystal form | II | I >> II | II >> I |

TABLE 4

| | Inorganic salt | NaCl | KCl |
|---|---|---|---|
| pH controlling agent (pH 6) | Addition concentration | 10 mM | 10 mM |
| | Addition amount | 0.6% | 0.7% |
| Potassium hydroxide | Addition concentration | 2.7 mM | 5.2 mM |
| | Addition amount | 0.2% | 0.3% |
| | Crystal form | II | II |
| Potassium carbonate | Addition concentration | 1.5 mM | 1.1 mM |
| | Addition amount | 0.2% | 0.15% |
| | Crystal form | II ≧ I | II |
| Dipotassium phosphate | Addition concentration | 2.9 mM | 2.3 mM |
| | Addition amount | 0.5% | 0.4% |
| | Crystal form | II | II |
| Potassium acetate | Addition concentration | 61.1 mM | 51.0 mM |
| | Addition amount | 6% | 5% |
| | Crystal form | II | II |
| Sodium bisulfite | Addition concentration | 4.8 mM (pH 5.5) | — |
| | Addition amount | 0.5% | |
| | Crystal form | II | |
| Sodium salicylate | Addition concentration | 15.6 mM (pH 5.6) | — |
| | Addition amount | 2.5% | |
| | Crystal form | I | |

TABLE 5

| pH controlling agent (pH 6) | Added salts | | | | NaCl | | |
|---|---|---|---|---|---|---|---|
| not added | Addition concentration | 0 mM | 5 mM | 10 mM | 17 mM | 34 mM | 86 mM |
| | Addition amount | 0% | 0.3% | 0.6% | 1% | 2% | 5% |
| | Crystal form | | | | II | | |
| Sodium hydroxide | Addition concentration | 1.8 mM | 1.8 mM | 1.8 mM | 1.8 mM | 1.8 mM | 1.8 mM |
| | Addition amount | 0.07% | 0.07% | 0.07% | 0.07% | 0.07% | 0.07% |
| | Crystal form | I | I >> II | II | II | II | II |
| Sodium carbonate | Addition concentration | 1.3 mM | 1.3 mM | 1.3 mM | — | — | — |
| | Addition amount | 0.13% | 0.13% | 0.13% | — | — | — |
| | Crystal form | I | I > II | I > II | — | — | — |
| Sodium acetate | Addition concentration | 45.7 mM | 45.7 mM | 45.7 mM | 45.7 mM | 45.7 mM | — |
| | Addition amount | 3.75% | 3.75% | 3.75% | 3.75% | 3.75% | — |
| | Crystal form | | | | II | | |
| Sodium citrate | Addition concentration | 4.8 mM | 4.8 mM | 4.8 mM | 4.8 mM | 4.8 mM | — |
| | Addition amount | 1.25% | 1.25% | 1.25% | 1.25% | 1.25% | — |
| | Crystal form | | | I >> II | | | |

Example 17

Stability test of crystal

An accelerated test was conducted at 50° C. for the crystals obtained in Examples 1 and 2 and the amorphous lyophilized products obtained in Comparative Example 3. Thereafter, a residual percentage of S-4661 was determined by HPLC method using an absolute correlation curve method. The crystal structure of the samples, amounts of the samples and residual percentage of S-4661 after the accelerated test (1 to 6 months later) are shown in Table 6. In the table, RH indicates a relative humidity, and lux indicates illuminance. It was confirmed that compared with the amorphous lyophilized products, the crystal of the present invention had a higher residual percentage after storage and, thus, more satisfactory storage stability. For example, under the condition of a high temperature, the maximum difference in the residual percentage between the crystal of the present invention and the amorphous lyophilized products was about 30%. Furthermore, in the crystal of the present invention, a change in appearance was not substantially observed even after the accelerated test.

Example 18

Stability test

An accelerated test was conducted at 50° C. for the crystalline lyophilized products obtained in Examples 3 to 8 and 10 to 14 and the amorphous lyophilized products obtained in Comparative Examples 1 to 3. Thereafter, a residual percentage of S-4661 was determined by an HPLC method using an absolute correlation curve method. The crystal structures of the samples, the amounts of the samples and the residual percentages after the accelerated test (after 0.5 month and after 1 month) are shown in Table 7. It was confirmed that compared with the amorphous lyophilized products, the lyophilized products of the present invention have more satisfactory storage stability.

TABLE 6

| | | Inner salt crystal | | Amorphous lyophilized preparation |
|---|---|---|---|---|
| Storage condition | Period | Example 13 Residual percentage | Example 14 Residual percentage | Comparative example 3 Residual percentage |
| In hermetic container at 50° C. | 1 M | 98.6% | 99.1% | 70.5% |
| | 2 | 98.1 | 99.1 | |
| | 3 | 97.2 | 99.5 | |
| In hermetic container at 40° C. | 1 M | 98.6 | 99.7 | 78.0 |
| | 2 | 97.8 | 99.5 | 76.4 |
| | 3 | 98.5 | 99.8 | |
| | 4 | 99.1 | 99.8 | |
| | 6 | 98.0 | 99.4 | |
| 40° C. RH 0% | 1 M | 99.5 | 99.4 | 88.1 |
| | 2 | 98.7 | 99.6 | 83.4 |
| | 3 | 97.7 | 99.5 | |
| | 4 | 99.7 | 99.6 | |
| | 6 | 98.7 | 99.1 | |
| 1800 lux | 1 M | 99.7 | 100 | 97.4 |
| | 2 | 99.3 | 100 | |
| | 3 | 99.0 | 99.0 | |

TABLE 7

| Sample (Example No.) | Crystal structure | Sample amount (mg/vial) | Residual percentage (storage at 50° C.) 0.5 month | 1 month |
|---|---|---|---|---|
| Example 3 | Type II | 250 | 99.1% | 99.6% |
| Example 4 | Type II | 250 | 99.9% | 98.0% |
| Example 5 | Type II | 250 | 100% | 99.3% |
| Example 6 | Type I | 250 | 98.0% | 99.3% |
| Example 7 | Type I | 250 | 100% | 100% |
| Example 8 | Type I | 250 | 98.6% | 98.7% |
| Example 10 | Type I | 250 | 98.5% | 98.5% |
| Example 11 | Type I | 250 | 97.9% | 97.2% |
| Example 12 | Type I | 250 | 98.3% | 97.8% |
| Example 13 | Type I | 250 | 99.4% | 99.9% |
| Example 14 | Type II | 250 | 98.9% | 99.5% |
| Comparative example 1 | Amorphous | 100 | 90.9% | 86.8% |
| Comparative example 2 | Amorphous | 250 | 96.7% | 93.7% |
| Comparative example 3 | Amorphous | 100 | 83.6% | 74.6% |

Examples 19 to 39

Effect of the addition of mannitol on reconstitution time and storage stability

In Examples 19 to 39, the effect of the addition of mannitol on reconstitution time and storage stability of the lyophilized preparation of the present invention was evaluated. Crystalline lyophilized products of S-4661 were obtained by using 500 mg of S-4661 (10 wt % aqueous solution) and varying the addition amount of mannitol as shown in Table 8. In each Example, NaCl was added in an amount of 15 mg (3 wt % with respect to S-4661). NaOH was added in an appropriate amount so that pH of the aqueous solution was 6. The first freezing step was performed by cooling the aqueous solution from +5° C. to −40° C. over 1 hour. The crystallization step was performed by repeating twice to 10 times the operation of cooling and warming the frozen solution in the range of −3° C. to −5° at a rate of about 10 K/hour over 5 to 10 hours, and then allowing the solution to stand at −5° C. or −10° C. for 5 to 10 hours. Vacuum drying was performed in the same manner as in Example 3.

The reconstitution time of the obtained crystalline lyophilized products was measured. The measurement of the reconstitution time was performed by adding the samples to 10 ml of water for injection, shaking the resulting mixture at 200 times/min., and measuring the period of time until the samples were completely dissolved. The results are shown in Table 8. Furthermore, each sample was tested with respect to storage stability at 50° C. in the same manner as in Example 18. The results are shown in Table 8. In the table, a change in appearance of each sample compared with the samples stored at −20° C. is shown in a parenthesis. − indicates no change, +− indicates a slight change, + indicates some change, ++ indicates a considerable change, and +++ indicates a significantly large change. It was confirmed that when mannitol was added, solubility was improved, and storage stability was not deteriorated.

TABLE 8

| Example No. | Mannitol addition amount | 0.5 month residual percentage(%) | 1 month residual percentage(%) | 2 months residual percentage(%) | 3 months residual percentage(%) | Reconstitution period |
|---|---|---|---|---|---|---|
| 19 | 0 mg | 99.5(−) | 99.5(−) | 97.6(−) | 97.4 | 1'02" |
| 20 | | 98.8(−) | 98.8(−) | 98.0(−) | 97.3 | 50" |
| 21 | | 98.7(−) | 98.8(−) | 99.7(−) | 99.5 | * |
| 22 | | * | 98.9(−~+−) | 98.1(−~+−) | 97.6 | 1'02" |
| 23 | 25 mg | 96.5(+) | 95.6(+) | 95.9(+) | 94.5 | 44" |
| 24 | | 96.5(+) | 95.2(++) | 94.5(+++) | 93.8 | 36" |
| 25 | | 96.9(+) | 95.7(+) | 94.8(+) | 93.8 | 36" |
| 26 | | 96.5(+) | 94.6(+) | 93.9(+~++) | 93.8 | 35" |
| 27 | 50 mg | 99.1(−) | 98.2(−) | 98.3(−) | 98.3 | 47" |
| 28 | | 98.8(−) | 97.4(−) | 97.6(−) | 97.2 | 34" |
| 29 | | 96.0(−) | 96.0(+−) | 94.3(+) | 93.1 | 30" |
| 30 | | 98.7(−) | 99.2(−) | 96.8(+−) | 96.5 | 25" |
| 31 | | 97.1(+) | 96.3(++) | 94.9(++~+++) | 93.9 | 31" |
| 32 | | 97.7(−) | 96.2(+−) | 96.7(+−) | 93.3 | 24" |
| 33 | | 96.5(+) | 94.7(+) | 94.9(+) | 94.7 | 30" |
| 34 | 75 mg | 99.9(−) | 99.5(−) | 98.7(−) | 98.0 | 23" |
| 35 | | 98.6(−) | 97.8(−~+−) | 96.6(+−~+) | 96.7 | 35" |
| 36 | | 100.7(−) | 100.2(−) | 99.0(−) | 99.1 | 25" |
| 37 | 100 mg | 99.2(−) | 98.0(−) | 98.7(−) | 97.7 | 26" |
| 38 | 150 mg | 99.5(−) | 99.0(−) | 99.3(−) | 99.0 | 26" |
| 39 | 200 mg | 99.3(−) | 98.9(−) | 98.8(−) | 99.4 | 26" |

*No data

INDUSTRIAL APPLICABILITY

According to the present invention, crystal of S-4661 excellent in storage stability and solubility and having a high industrial applicability can be obtained. Furthermore, the present invention also provides a lyophilized preparation containing the crystal. It is not only easy to ensure sterility and remove particulate matters in the lyophilized preparation, but also the lyophilized preparation is excellent in storage stability and solubility. S-4661 is useful as an antimicrobial drug, and orally or parenterally administered. The crystal of S-4661 of the present invention and the lyophilized preparation containing the crystal are particularly useful as an injection.

We claim:
1. A lyophilized crystalline preparation comprising a crystal of (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid represented by the following formula:

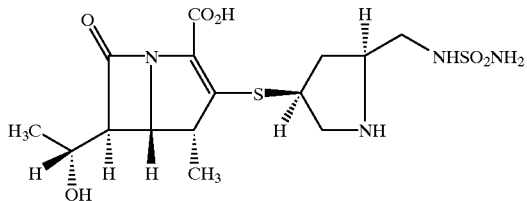

or an inner salt thereof, wherein the crystal is a Type I crystal, which has a powder X-ray diffraction pattern having a primary peak at a diffraction angle (2θ)=7.32, 14.72, 16.62, 20.42, 21.1, 22.18, 23.88 and 29.76 (degree); or a Type II crystal, which has a powder X-ray diffraction pattern having a primary peak at a diffraction angle (2θ)=6.06, 12.2, 14.56, 17.0, 18.38, 20.68, 24.38, 24.60, 25.88 and 30.12 (degree); or wherein the lyophilized crystalline preparation comprises a mixture of the Type I crystal and the Type II crystal;

wherein the lyophilized crystalline preparation exhibits an increased storage stability compared to a lyophilized amorphous preparation of (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid, and wherein the lyophilized amorphous preparation is prepared by cooling an 8 percent aqueous solution of (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid to −30° C. over 1 hour and then vacuum drying the frozen solution, and wherein said storage stability is measured for at least one month either in a hermetic container at 40° C. or in a hermetic container at 50° C., or at zero percent relative humidity at 40° C.; and wherein the lyophilized crystalline preparation may further comprise at least one of the following compounds selected from the group consisting of mannitol, an inorganic salt, and a pH adjusting or controlling agent.

2. A crystal of (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid represented by the following formula:

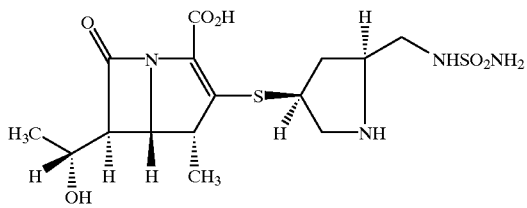

or an inner salt thereof, wherein a powder X-ray diffraction pattern of the crystal has a primary peak at a diffraction angle (2θ)=7.32, 14.72, 16.62, 20.42, 21.1, 22.18, 23.88 and 29.76 (degree).

3. A crystal of (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid represented by the following formula:

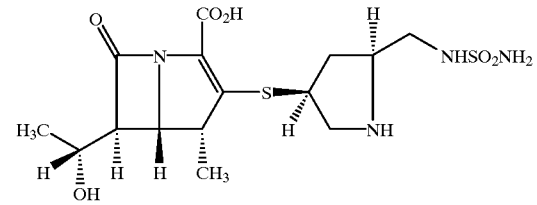

or an inner salt thereof, wherein a powder X-ray diffraction pattern of the crystal has a primary peak at a diffraction angle (2θ)=6.06, 12.2, 14.56, 17.0, 18.38, 20.68, 24.38, 24.60, 25.88 and 30.12 (degree).

4. A process for producing a crystal of (1R,5S,6S)-6-[(1R)-1-hydroxyethyl]-2-[(3S, 5S)-5-sulfamoylaminomethyl-1-pyrrolidin-3-yl]thio-1-methyl-1-carba-2-penem-3-carboxylic acid represented by the following formula:

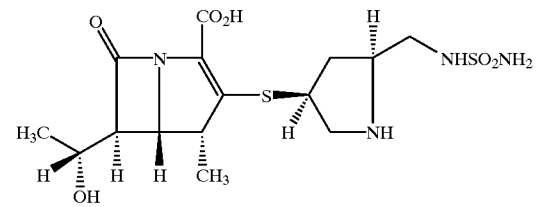

or an inner salt thereof, wherein the crystal is a Type I crystal, which has a powder X-ray diffraction pattern having a primary peak at a diffraction angle (2θ)=7.32, 14.72, 16.62, 20.42, 21.1, 22.18, 23.88 and 29.76 (degree); or a Type II crystal, which has a powder X-ray diffraction pattern having a primary peak at a diffraction angle (2θ)=6.06, 12.2, 14.56, 17.0, 18.38, 20.68, 24.38, 24.60, 25.88 and 30.12 (degree); or wherein the crystal is a mixture of the Type I crystal and the Type II crystal; the process comprising the steps of freezing, by cooling to −20° C. or lower, an aqueous solution comprising (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid;
warming the frozen solution to 0 to −10° C.; and
cooling and then warming, or warming and then cooling, the frozen solution at least twice between 1 and 5 K while remaining within the temperature range of 0 to −10° C., wherein the warming rate and cooling rate is 8 to 12 K/hour; wherein by the process of warming and then cooling, or cooling and then warming, the frozen solution results in crystallization of the (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid.

5. The lyophilized crystalline preparation according to claim 1, wherein the preparation comprises the mixture of the Type I crystal and the Type II crystal.

6. The lyophilized crystalline preparation according to claim 1, wherein the pH adjusting or controlling agent is selected from the group consisting of NaOH, $Na_2CO_3$ and $NaHCO_3$.

7. A process according to claim 4, wherein pH of the aqueous solution is in a range of 5.8 to 6.2.

8. A process according to claim 4, wherein the aqueous solution comprises at least one compound selected from the group consisting of NaOH, $Na_2CO_3$ and $NaHCO_3$.

9. A process according to claim 8, wherein the aqueous solution further comprises an inorganic salt.

10. A process according to claim 9, wherein the inorganic salt is present in an amount of 0.02 to 0.13 moles on the basis of 1 mole of (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid.

11. A process according to claim 9, wherein the inorganic salt is NaCl.

12. A process according to claim 4, wherein the aqueous solution further comprises mannitol.

13. A process according to claim 12, wherein the mannitol is present in an amount of at least 15 parts by weight on the basis of 100 parts by weight of (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid.

14. A process according to claim 13, wherein the mannitol is present in an amount of 15 to 50 parts by weight on the basis of 100 parts by weight of (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid.

15. A process according to claim 4, wherein the frozen solution is cooled and warmed in a temperature range of 1 to 3 K.

16. A process according to claim 4, wherein the frozen solution is cooled and warmed twice to 10 times.

17. A process according to claim 4 further comprising the step of allowing the frozen solution to stand at −3 to −10° C. for 1 to 10 hours.

18. The process according to claim 4, further comprising subjecting the crystal to vacuum drying, so as to obtain a lyophilized preparation of the crystal.

19. The lyophilized crystalline preparation according to claim 1, wherein the crystal is the Type I crystal and wherein the preparation does not contain the Type II crystal.

20. The lyophilized crystalline preparation according to claim 1, wherein the crystal is the Type II crystal and wherein the preparation does not contain the Type I crystal.

* * * * *